United States Patent [19]

Bjelkhagen et al.

[11] Patent Number: 5,014,709
[45] Date of Patent: May 14, 1991

[54] METHOD AND APPARATUS FOR HIGH RESOLUTION HOLOGRAPHIC IMAGING OF BIOLOGICAL TISSUE

[75] Inventors: Hans Bjelkhagen, Chicago, Ill.; Marc D. Friedman, Watertown, Mass.

[73] Assignee: Biologic Systems Corp., Mundelein, Ill.

[21] Appl. No.: 365,336

[22] Filed: Jun. 13, 1989

[51] Int. Cl.$^5$ .............................................. A61B 6/00
[52] U.S. Cl. .................................. 128/654; 128/665; 350/3.6; 356/347
[58] Field of Search ................... 128/653 R, 665, 654; 350/3.6; 356/347

[56] References Cited

U.S. PATENT DOCUMENTS

| | | | |
|---|---|---|---|
| 3,979,263 | 9/1976 | Bucalo | 128/749 |
| 4,336,809 | 6/1982 | Clark | 128/665 |
| 4,643,514 | 2/1987 | Raviv et al. | 356/347 |

FOREIGN PATENT DOCUMENTS 0038970  2/1986  Japan .................................... 350/3.6

OTHER PUBLICATIONS

Tokuda et al., "Holocamera for 3-D Micrography of the Alert Human Eye" Applied Optics, vol. 19, No. 13, Jul. 1980 pp. 2219-2225.
Hofstetter et al., "Holographic Laser Interferometry for Detection of Tissue Changes in the Rabbit Urinary Bladder", Laser & Elecktro-Optik, vol. 10, No. 3, Sep. 1978, pp. 30-31.
Lekhtsier, "Holographic Microscopay in Measurement Techniques", Meas. Tech (USA), vol. 21, No. 9, Sep. '78, pp. 1199-1204.
Yonemura et al., "Endoscopic Hologram Interferometry Using Fiber Optics", Applied Optics, vol. 20, No. 9, May 1981, pp. 1664-1667.
Bally et al., "Gradient Index Optical Systems in Holographic Endoscopy" Applied Optics, vol. 23, No. 11, Jun. '84, 1725-1729.
"Endoholography in Medicine", Journal of Laser Applications, Fall, 1988, pp. 40-44.
"Endoholographic Imaging", 100SPIE, vol. 1068, Catheter-Based Sensing and Imaging Technology (1989), pp. 100-107.
"Holographic High Resolution Endoscopy through Optical Fibers", by H. I. Bjelkhagen, M. D. and Epstein M. Friedman, Biomedical Engineering, Northwestern University, Evanston, Illinois, 9 pages.
"Holography Captures Living Tissue", New Scientist, Aug. 11, 1988, p. 32.
"Holography Brings High Resolution to Endoscopy", OE Reports, Feb., 1989, p. 5.
"The Holographic Endoscope", Holographics International, Summer, 1988, p. 21.
"White-Light Reconstruction of Holographic Images Using the Lippmann-Bragg Diffraction Effect", Physics Letters, Mar., 1966, vol. 20, No. 4, pp. 368-370.
"Image Contrast Arising from Specimen in Motion in Holographic Imagery", by Ernest Feleppa, Riverside Research Institute, pp. 203-207.
"Endoholography, The Use of Holography in Endoscopy" by Gil Raviv, Northwestern University, Jun. 1986, pp. i-x and 1-160.

Primary Examiner—Ruth S. Smith
Attorney, Agent, or Firm—Welsh & Katz, Ltd.

[57] ABSTRACT

Apparatus and methods for high resolution holographic recordation and microscopic examination of the holographic image of biological tissue. A single beam Denisyuk holographic recordation of the biological tissue is obtained with direct contact or close proximity to the tissue. Contrast enhancement by staining with a dye selected to maximize absorption of the light frequency used to record the hologram is used to improve contrast and resolution. A liquid interface is formed between the recording film and the subject tissue to improve image quality and resolution. The resulting high resolution three dimensional holographic images may be examined under microscope magnification for such applications as medical biopsy.

78 Claims, 4 Drawing Sheets

FIG. 1A

METHOD AND APPARATUS FOR HIGH RESOLUTION HOLOGRAPHIC IMAGING OF BIOLOGICAL TISSUE

The present invention relates generally to the field of examination of biological tissue and more particularly to apparatus and methods for high resolution holographic recordation and examination of biological tissue.

Various prior art techniques for examination of biological tissue are known in the prior art for use in such applications as medical diagnosis. These techniques suffer from a number of deficiencies and limitations. In one approach, a specimen for biopsy is exercised and examined, typically under a microscope. This approach suffers from various risks to the patient and requires removal of the cells from their live environment. In addition, it is difficult and expensive to preserve the specimen for future reexamination. Other prior techniques include the use of motion picture recordation and various still photography techniques which have limited resolution and which only provide 2-dimensional visualization of the desired structures. Another method employs x-ray scanning, but this also has low resolution, the equipment is expensive to purchase and maintain, and radiation exposure may prove harmful to the subject structure in the case of living tissue.

Medical applications in holography are also known in the art, including holographic endoscopic techniques wherein a hologram is made of internal cavities and passageways of the human body. Such holograms are formed when coherent light, typically from a laser, produces a record of a light interference pattern on a light sensitive recording medium such as photographic film. The light which strikes the film to produce the hologram is the sum of two beams: One, the reference beam, is derived directly from the laser; and the other, the object beam is light from the same laser source after it has been scattered from the object. Thus, the image recorded on the film is the interference pattern of the reference and object beams. When the exposed film is processed and illuminated by an appropriate light beam, the beam is diffracted to produce an image of the original object, faithfully reproducing all of its three dimensional features. However, such prior art endoscopic holograms are limited in resolution and are not suitable for microscopic examination.

It is accordingly an object of the present invention to provide novel methods and apparatus for holographic recordation and examination of biological tissue suitable for microscopic examination.

It is another object of the invention to provide novel methods and apparatus for holographical recordation and examination of biological tissue using close proximity holographic recording and contrast enhancement to obtain high contrast, high resolution holograms.

It is yet another of the invention to provide novel methods and apparatus for holographic recordation and examination of biological tissue using contact holography with a liquid interface to provide high resolution, high quality holograms suitable for microscopic examinations and long term preservation for re-examination.

Accordingly, in accordance with one embodiment of the invention, there is provided apparatus for holographic examination of the features of selected biological tissue, including a light sensitive recording medium such as a photographic film and means for producing contrast enhancement of selected portions of the biological tissue, such as a dye. Placement means is provided for positioning the recording medium within approximately one millimeter or less of the selected biological tissue, and a source of coherent light, such as a laser, is provided for directing a beam of coherent light on to the recording medium and the selected biological tissue to permit recording of a hologram of the selected biological tissue.

BRIEF DESCRIPTION OF THE DRAWINGS

The invention, together with further objects and advantages thereof may be understood by reference to the following description taken in conjunction with the accompanying drawings.

DETAILED DESCRIPTION OF THE PREFERRED EMBODIMENT

Figure 1A:
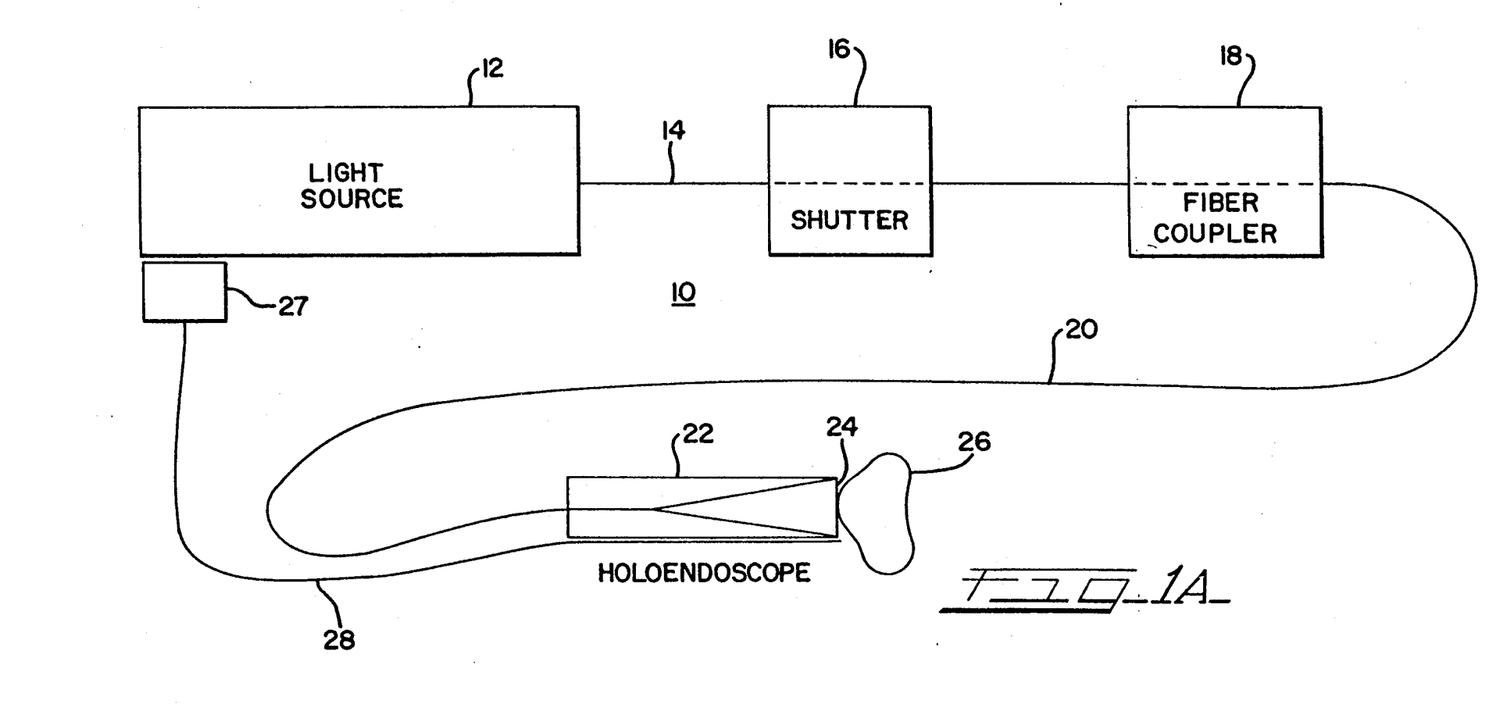
FIG. 1A is a generalized block diagram illustrating a specific embodiment of holographic recording and examination apparatus with external light source in accordance with the invention.

In FIG. 1a, there is illustrated a generalized block diagram of a specific embodiment of a holographic examination apparatus 10 in accordance with the invention. A laser or other source of coherent light 12 directs a coherent beam 14 of light of selected frequency (i.e., in the rang from infrared to ultraviolet) through an optional shutter 16 which is used to control the light beam by selectively passing or interrupting the beam 14. When the shutter 16 is open, the beam 14 passes through the shutter 16 to an optical fiber coupler 18 where it is coupled to an optical fiber 20. The shutter 16 may include timing apparatus and permits pulsing the light source and control of the time during which light is allowed to pass (i.e., control exposure time). A pulsed or Q-switch laser may also be used to permit pulsing of the light source without use of a shutter. In the preferred embodiment, the optical fiber 20 is a single mode fiber which may be rigid or flexible as needed and which transmits the coherent light to a placement device 22. The divergent coherent light from the optical fiber 20 is directed onto a light sensitive recording medium 24, (i.e., forming a reference beam).

The light sensitive recording medium 24, such as photographic film, photopolymer, electronic recording medium such as high resolution CCD array, etc., is held by the placement device 22 in direct contact with or in close proximity (i.e., typically within approximately 1 mm) to the subject biological tissue 26, as shown. The light sensitive recording medium is chosen to be particularly sensitive to the frequency of the coherent light of the light source 12. The coherent light is also directed onto the subject biological tissue 26 (i.e., the hologram object) typically by passing through the light sensitive recording medium 24 (i.e., thereby forming an object beam). This light is then scattered by the biological tissue 26 back to the light sensitive recording medium 24 forming an interference pattern with the reference beam which is recorded as a hologram by the light sensitive recording medium 24.

The placement device 22 may be designed to function within body cavities and passageways, for example, as a holographic endoscope (i.e., holoendoscope), or for use on surface tissue. Thus, in-vivo holograms of live tissue may be obtained. A tube 28 may be provided to channel a contrast enhancing medium, such as a dye or powder from a reservoir 27 to the placement device 22 to permit contrast enhancement (e.g., applying a dye to stain the subject biological tissue), as shown. Such contrast enhancement enables high contrast holographic recording of desired features of the biological tissue. The light frequency and dye are chosen to maximize absorption by cell structures (e.g., organelles) of interest.

The reservoir 27 and tube 28 may also be utilized to apply a transparent liquid such as water to the surface of the biological tissue to create a thin liquid interface between the light sensitive recording medium and the biological tissue. Preferably, when the liquid interface is used, all air spaces should be eliminated. Such a liquid interface provides index matching to reduce reflections and enhance the quality of holograms made in contact with the biological tissue. When contact holograms are recorded using film, the film emulsion preferably is faced toward the light source with the substrate in contact with the tissue or liquid layer, thereby preventing the liquid or tissue from affecting the emulsion.

The optical fiber 20 may also comprise multiple fibers to permit multiple colors (e.g., from three lasers) of light to be used to obtain color holograms. For example, three fibers, one carrying red light, one carrying blue light, and one carrying green light, can be used to obtain a full color hologram. Alternatively, multiple colors of light can be transmitted through a single optical fiber. The intensity of each color can be adjusted to create desired effects or to match film sensitivity characteristics.

Figure 1B:
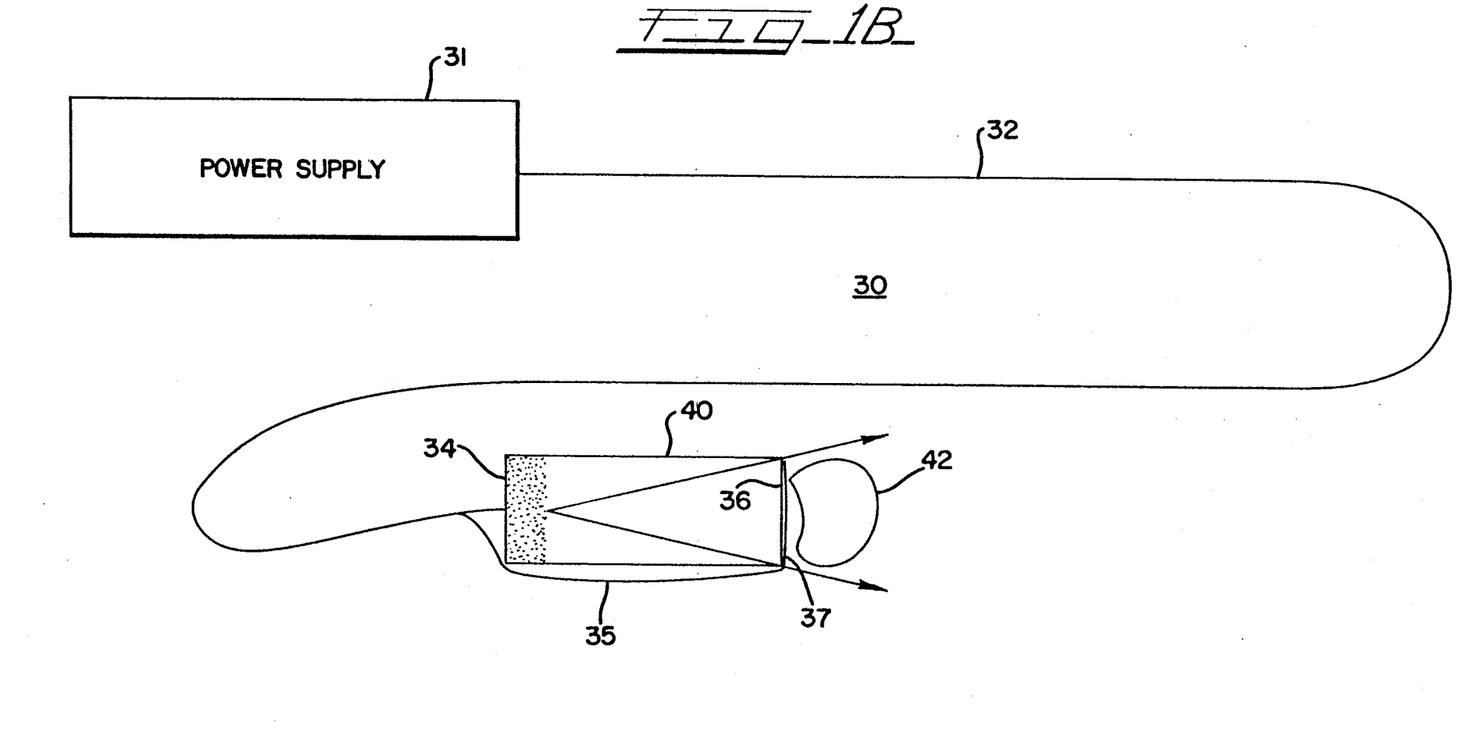
FIG. 1B is a generalized block diagram illustrating another embodiment of holographic recording and examination apparatus with self-contained light source in accordance with the invention.

An embodiment of a holographic examination apparatus 30 in which a self-contained light source is used is illustrated in the generalized block diagram of FIG. 1B. A power supply 31 supplies power which is coupled to a coherent light source 34 (e.g., laser diode) within a placement device 40 via a cable 32. The cable may also optionally include a tube for carrying a contrast enhancing dye and a means for applying a liquid interface material, to be applied to the subject biological tissue 42 and other controls or features such as an optical viewing fiber. The optical viewing fiber can be provided to aide the operator in maneuvering the placement device to the desired location. A control line 35 may be provided to control a cover, such as a balloon-like rubber cover or shutter 37, which is removable by the control line 35 to permit cOntrol of ambient light fogging of the light sensitive recording medium.

The light source 34 generates coherent light which is directed onto the light sensitive recording medium 36 and onto the subject biological tissue 42. The placement device 40 holds the light sensitive recording medium 36 in close proximity or direct contact with the tissue 42. If direct contact is utilized, a liquid interface may be added to improve the quality of the resultant hologram. The light source 34 may also comprise multiple color light generating sources (e.g., 3 laser diodes of different colors) to permit color holograms to be recorded. The placement device 40 may optionally be configured to be placed at a desired location by another placement device such as a conventional endoscope which typically has self-contained viewing fibers, means for carrying such devices as a holographic placement device 22, 40, and mechanisms suitable for applying a contrast enhancing dye and a liquid interface.

Figure 2A:
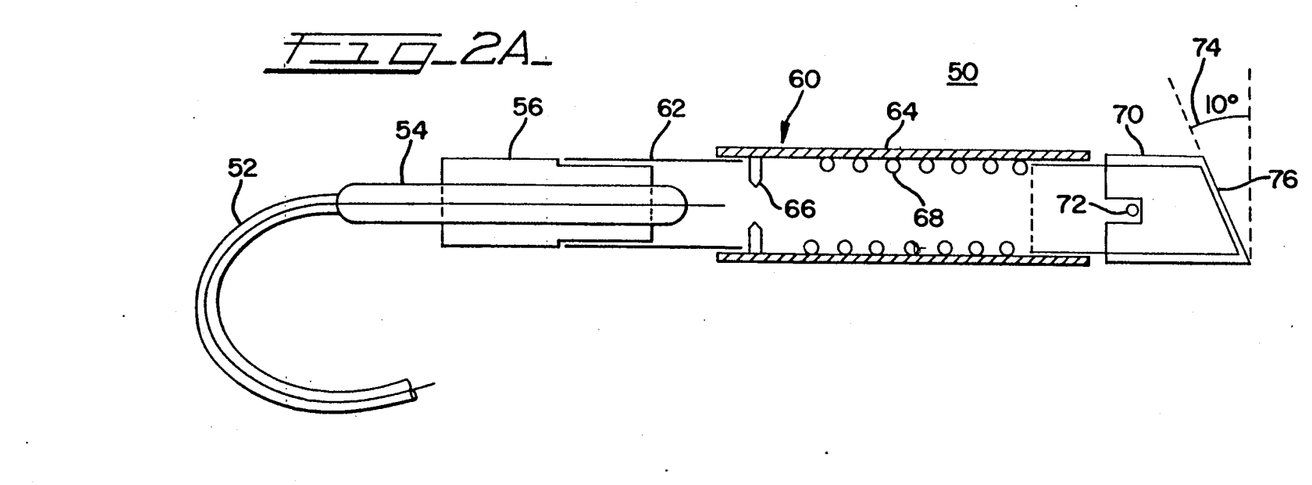
FIG. 2A is a detailed diagram illustrating a specific embodiment of a holoendoscope in accordance with the invention.

Referring now to FIG. 2A, there is shown a detailed diagram of a holoendoscope 50 in accordance with the invention. The holoendoscope is a specific embodiment of the placement device 22 of FIG. 1A designed to be particularly suitable for internal holographic examination although it is also suitable for holographic examination of external tissue. The holographic endoscope 50 comprises a sheathed optical fiber 52 (e.g., in the illustrated embodiment, single-mode fiber with a four micron core diameter for green argon laser light, 514.5 mm wavelength) which couples externally generated coherent light to the holoendoscope 50. The optical fiber 52 is fitted into a fiber holding rod 54 which is mounted in a fiber holder 56, both composed of brass in the preferred embodiment, which holds the optical fiber 52 in place in the holoendoscope 50, as shown. The fiber holder 56 is mounted in a telescoping housing 60 composed in the illustrated embodiment of an inner segment 62 and an outer segment 64 of stainless steel tubing having a diameter of approximately 10 mm. The telescoping sections 62, 64 provide an adjustable length housing by permitting the tubes to slide over one another.

Inside the housing 60 is mounted a diaphragm 66, as shown, to limit the beam width and control reflection scattering within the housing 60. The diaphragm 66 and inner surface of the housing 60 is also a light baffle designed to minimize internal reflections by means of a reflection reducing spring 68 and, for example, by covering the spring 68 and innersurface with a flat black coating. A film cartridge 70 is provided which is removably mounted on the end of the housing 60, as shown. In the illustrated embodiment, the cartridge 70 comprises a segment of tubing configured to form a friction fit with the inside diameter of the housing 60 with a positioning post 72 mounted on the inside of the housing for guiding the cartridge to the proper position. A disk of film 76 (e.g., light sensitive recording medium) is mounted at an angle 74 on the end of the film cartridge, as shown. In the illustrated embodiment of FIG. 2A, the holoendoscope 50 has an overall length of approximately 86 mm.

Figure 2B:
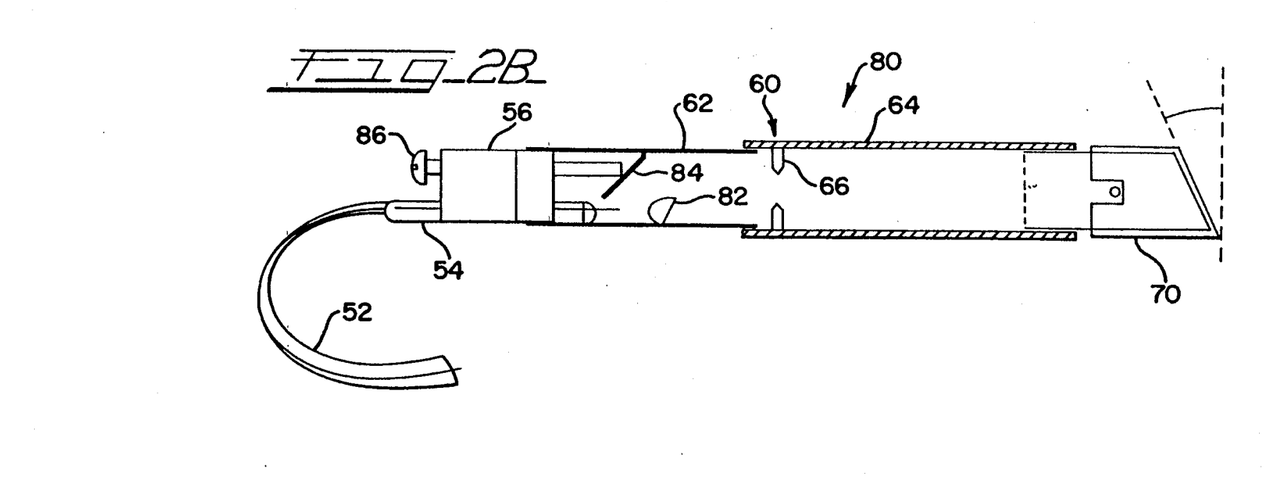
FIG. 2B is a detailed diagram illustrating another embodiment of a holoendoscope with a folded light beam in accordance with the invention.

An embodiment of a holoendoscope 80 in which the light beam is folded to permit a shorter construction allowing access to smaller places within a biological body is shown in FIG. 2B. In the holoendoscope 80, a fixed mirror 82 and an adjustable mirror 84 are configured to reflect the beam from the optical fiber 52 between them and then toward the film cartridge 70. This permits the light beam to diverge over a longer distance without extending the length of the housing 60. An adjustable screw 86 permits adjustment of the mirror 84. The remainder of the structure of the holoendoscope 80 is substantially similar to that of the holoendoscope 50 of FIG. 2A.

In use, the holoendoscope 50, or other placement device such as shown in FIG. 1A, is located so as to place the film 76 in contact or near contact with the selected biological tissue which is the subject of the holographic examination. The holoendoscope 50 is then used to record a single beam hologram in which the coherent light from the fiber 52 illuminates the film 76 (e.g., with a Gaussian intensity distribution of light) and simultaneously, illuminates the tissue with some of the light which passes through the film (i.e., forming a Denisyuk hologram). As a result, the scattered light from the tissue forms an interference pattern with the illuminating reference beam at the film 76 such that a reflection hologram of the tissue is recorded by the film 76 with a very high resolution. Other configurations, such as an evanescent hologram may be used to obtain the single beam hologram. In addition, multiple beam holography may also be used.

To obtain a sufficiently high resolution to permit microscopic examination of the reflection hologram generated, the film 76 is preferably in very close proximity when the hologram is recorded, i.e., within approximately 1 mm. The film cartridge 70 preferably holds the film 76 in an angle 74 (e.g., 10 degrees in the illustrated embodiment) to the normal of the holoendoscope 50. This allows the illumination to be offset from the observer when reconstructing the hologram.

The film 76 is cut into suitable sized disks of film (approximately 8 mm in diameter in the illustrated embodiment) by using a circular punch cutter on commercial high resolution film suitable for recording high quality holograms. The resulting film disk is then loaded into the cartridge 70 under suitable safelight conditions. In the illustrated embodiment, the coherent light source may be an Argon ion laser or (e.g., a 514.5 nm laser, Model No. 164 marketed by Spectra Physics) or a Krypton ion laser. Suitable film includes, for example, red sensitive film Agfa Holotest 8E 75 HD T3 for use in conjunction with a krypton laser source and green sensitive Ilford SP 672 for use in conjunction with an Argon laser.

To substantially improve the suitability of the recorded holographic images holograms of the selected biological tissue for microscope examination, contrast enhancement may be utilized. Contrast enhancement may be provided by such means as application of a powder or application of a dye to stain desired features of the biological tissue, injection of a substance which enhances desired features of the biological tissue, generating motion in the desired portion of interest of the biological tissue, etc. In the illustrated embodiment, a dye selected to correspond in absorption characteristics with the frequency of the laser light used dramatically improves the contrast of the resulting hologram. Thus the dye is selected to maximize absorption at the frequency of the laser light used in order to maximize contrast. Many dye/laser combinations are suitable for contrast enhancement. Commercially available (e.g., from Aldrich Chemical Company) dyes in combination with the appropriate laser have been found to provide excellent contrast enhancement, including the following: (1) trypan blue, methylene blue, or toluidine blue o provide strong red absorption in combination with a Krypton laser, and (2) phloxine b, rose bengal, new fuchsin provide strong green absorption in combination with an Argon laser. These dyes, which have been approved by the FDA for internal human use, have shown excellent fastness properties for staining while providing dramatic contrast improvement in the hologram produced by the holoendoscope 50. This contrast enhancement also enhances the resolution obtainable in the hologram image.

Contrast enhancement may enhance contrast of internal features below the surface of the subject biological tissue as well as surface features. Contrast enhancement of tissue features or organelles below the surface may be accomplished by numerous means. For example, a penetrating dye may be used followed by a wiping or washing of the surface, or a conventional dye mixed with a penetrating carrier such as Dimethyl Sulfoxide (DMSO) may be used to penetrate into the tissue. Optionally, a dye may be injected below the surface, or a contrast enhancing agent may be injected into the blood stream and absorbed by the subject tissue. To enhance blood vessels, etc., a contrast enhancing agent can simply be injected into the blood stream enabling three dimensional images of the blood vessels, capillaries, etc. In addition, a long wavelength of coherent light may be selected to enhance penetration through the selected tissue to maximize depth. Thus, for example, red or infrared light may be used to obtain penetration to 1 mm or more into the tissue enabling recording of enhanced features within the tissue. The resulting hologram provides a three dimensional holographic image of the tissue which permits microscopic examination of features at any depth within the depth of penetration of the recorded holograms.

In addition to the formation of holograms of biological tissue, the apparatus described herein may also be utilized to record holographic interferograms which is a holographic image recording which shows the effect of motion, displacement, or deformation, or which shows the contour of an object. A feature or portion of the biological tissue in motion may be characterized by formation of an interferogram recorded by two consecutive pulses of the coherent light separated by a predetermined time interval. This may be accomplished, for example, by pulsing the laser source 12 or by opening and closing the shutter 16 (see FIG. 1A). The reconstructed image from this type of interferogram exhibits dark and bright interference fringes which have a spacing characteristic of the displacement of the structure during the interval between laser pulses. Using this technique, it is possible to examine detailed deformation processes and dynamic motion of structures, and it is possible to produce a hologram with fringes corresponding to the contour of the object recorded.

A time averaged interferogram of the biological tissue may be obtained by providing one pulse of coherent light which has a pulse time duration longer than one time period of any vibrational motion or long enough to cause portions with other motion (e.g., flowing blood) to appear darker due to phase change during recording. This resulting interferogram will show dark and light rings characteristic of vibration or will provide effective contrast enhancement of moving features of the biological tissue (e.g., blood moving in blood vessels, motion of living tissue, etc.).

The holograms obtained using the holoendoscope 50 in combination with staining may be viewed during reconstruction by microscope examination. Reconstruction may be obtained by illuminating the hologram with a laser or broadband light thereby generating a high contrast, high resolution, three dimensional holographic image. The high contrast and high resolution of the holographic image obtained permits large magnifications for such examination purposes as biopsies. These biopsy holograms may be stored for long periods of time and may be reexamined at a later time without degradation. The holograms obtained may also generate magnified images by reconstruction using a wavelength of light for reconstruction which is longer than the wavelength of the light used to record the hologram. In addition, by chemical or other processing, before, during or after development, shrinkage of the film emulsion may be controlled to control the color of the resulting reconstructed holographic image (e.g., a red image is often most desirable) regardless of the color used to record the hologram.

Figure 3:
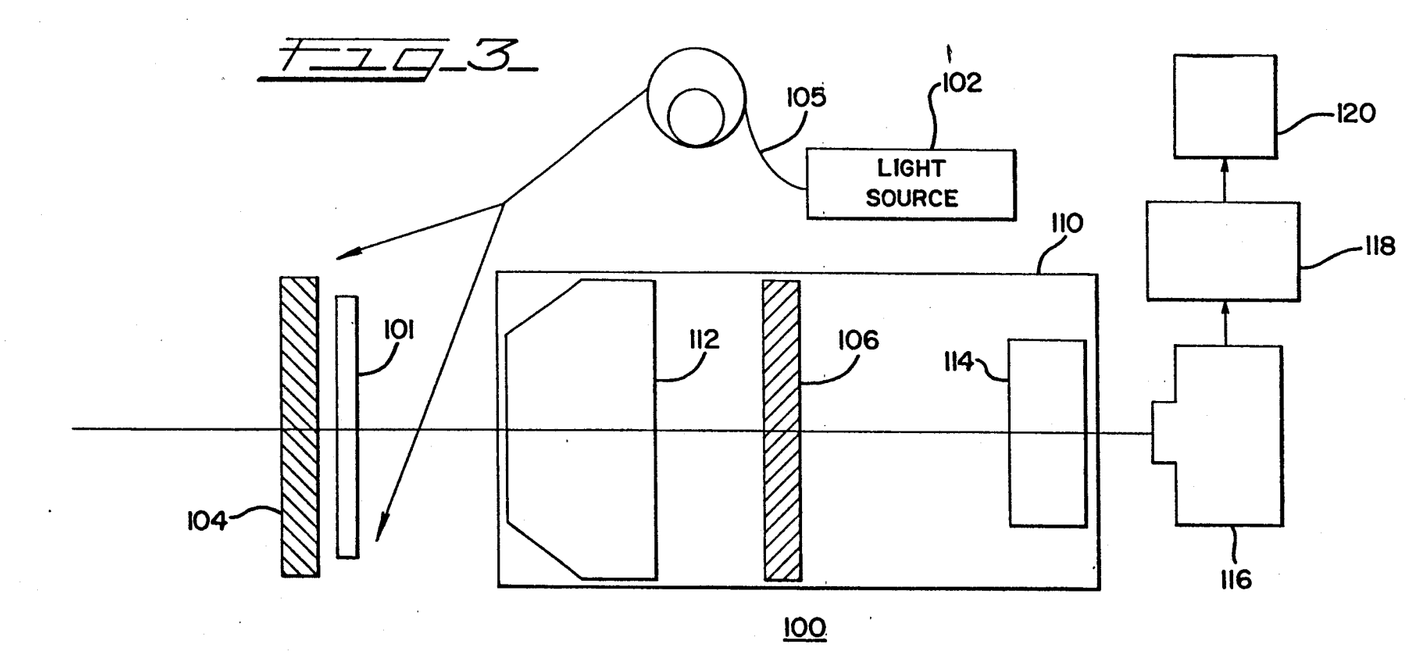
FIG. 3 is a diagram of a specific embodiment of the microscopic examination hologram reconstruction configuration in accordance with the invention.

FIG. 3 illustrates a specific embodiment of a structure 100 for reconstruction and microscopic examination of the holoendoscope generated hologram 101. The hologram 101 is illuminated by a light source 102 which may be laser light, broad band light such as light filtered to a selected broad color band, or white light. Because the hologram is recorded in contact or in close proximity to the tissue, a high resolution image can be obtained with white light reconstruction while also obtaining the improved image quality of broadband reconstruction. An optical fiber 105 may be used to direct the light onto the reflection hologram 101. Optionally, a polarizer 104 may be mounted behind the hologram 101, as shown. A microscope structure 110 is provided for examination of the holographic image including an objective lens 112 and an eye piece lens 114, as shown. Optionally, a polarizer 106 may be provided in conjunction with the microscope structure 110 placed anywhere between the viewing means 116 and the hologram 101, for example, between the lense 112 and the lense 114, as shown. By arranging the polarizers 104, 106 with crossed polarization (i.e., at 90° to each other) reflections from behind the hologram 101 may be eliminated. The structure 100 permits high magnification examination of the hologram 101 by a viewing means 116. The viewing means 116 may simply be the eye of viewer, or may be a viewing device such as an electronic camera for converting the image to electronic signals. These electronic signals may be coupled, as shown, to an image processor 118 for electronic processing and analysis of the signals or directly to a monitor 120 for display. Electronic processing may include, for example, digital filtering, contrast enhancement, frequency analysis, 3-D rotation, digital magnification, threshold analysis, etc.

Specific embodiments of the holographic recording and examination methods and apparatus according to the invention have been described for the purpose of illustrating the manner in which the invention may be made and used. It should be understood that implementation of other variations and modifications of the invention in its various aspects will be apparent to those skilled in the art, and that the invention is not limited by the specific embodiments described. It is therefore contemplated to cover by the present invention any and all modifications, variations or equivalents that fall within the true spirit and scope of the basic underlying principles disclosed and claimed herein.

What is claimed is:

1. Medical apparatus for holographic examination of features of selected biological tissue, comprising:
   a light sensitive recording medium;
   means for producing contrast enhancement of selected portions of the selected biological tissue;
   placement means coupled to the means for producing contrast enhancement for positioning the recording medium within approximately 1 mm or less of the selected biological tissue; and
   a coherent light source for directing a beam of coherent light onto the recording medium and the selected biological tissue whereby a hologram of the selected biological tissue is recorded.

2. The apparatus of claim 1 wherein the coherent light source is a laser means for generating laser light.

3. The apparatus of claim 2 wherein the laser means is at least one diode laser incorporated with the placement means.

4. The apparatus of claim 1 wherein the coherent light source comprises a plurality of different colored lasers which enable formation of a full color hologram.

5. The apparatus of claim 1 wherein the coherent light source comprises means for pulsing the light source at least twice to generate at least two light pulses separated in time to generate a holographic interferogram.

6. The apparatus of claim 1 wherein the placement means has dimensions sufficiently small to permit passage through the passageways of a biological body.

7. The apparatus of claim 1 wherein the placement means comprises means for covering the light sensitive recording medium and means for removing the means for covering.

8. The apparatus of claim 1 wherein the coherent light source comprises an external laser coupled to an optical fiber for directing the coherent light to the placement means and onto the recording medium.

9. The apparatus of claim 1 wherein the means for producing contrast enhancement comprises means for staining the selected biological tissue with a dye.

10. The apparatus of claim 9 wherein the dye has absorption spectrum characteristics corresponding to the frequency of the coherent light beam to maximize absorption of the coherent light by the dye.

11. The apparatus of claim 1 wherein the placement means further comprises means for applying a liquid layer on the selected biological tissue.

12. The apparatus of claim 1 wherein the placement means comprises a set of mirrors for reflecting the coherent light between each mirror and onto the light sensitive recording medium.

13. The apparatus of claim 1 wherein the placement means comprises a telescoping housing having an internal light baffle.

14. The apparatus of claim 13 wherein the placement means further comprises a film cartridge adapted to be removably mounted on the telescoping housing.

15. The apparatus of claim 14 wherein the film cartridge is adapted to hold the light sensitive recording medium at a non-perpendicular angle to the beam of coherent light.

16. The apparatus of claim 1 wherein the placement means is structurally configured to permit placing the light sensitive recording medium in direct contact with the selected biological tissue.

17. The apparatus of claim 1 further comprising means for illuminating the hologram with selected light to reconstruct a holographic image of the selected biological tissue.

18. The apparatus of claim 17 further comprising microscope means for examining the holographic image.

19. The apparatus of claim 18 further comprising a pair of polarizers arranged with crossed polarization with one polarizer in front and the other behind the hologram during illumination to eliminate undesirable reflections.

20. The apparatus of claim 17 wherein the selected light is white light.

21. The apparatus of claim 17 further comprising electronic viewing means for converting the holographic image into corresponding electronic signals and means for displaying the image responsive to the corresponding signals.

22. The apparatus of claim 21 further comprising processing means for performing image processing of the corresponding electronic signals.

23. The apparatus of claim 17 wherein the selected light is broadband filtered light.

24. The apparatus of claim 17 wherein the selected light has a longer wavelength than the coherent light used to record the hologram thereby reconstructing a magnified holographic image.

25. The apparatus of claim 1 further comprising means for controlling the time that the coherent light is directed onto the light sensitive recording medium.

26. A method for holographic examination of biological tissue comprising the steps of:
 positioning a light sensitive recording medium within approximately 1 mm or less of the biological tissue;
 contrast enhancing selected features of the biological tissue;
 directing a coherent light beam onto the light sensitive recording medium and the biological tissue; and
 exposing the light sensitive recording medium to a resulting interference pattern, thereby recording a hologram of the biological tissue.

27. The method of claim 26 wherein the step of exposing comprises the step of exposing the recording medium for an extended period of time sufficient to form a holographic interferogram of the selected biological tissue.

28. The method of claim 26 wherein the step of directing the coherent light beam comprises pulsing the light source at least twice to generate at least two light pulses separated in time to generate a holographic interferogram.

29. The method of claim 26 further comprising the step of applying a liquid layer on the selected biological tissue to form a liquid interface between the recording medium and the biological tissue.

30. The method of claim 26 wherein the step of contrast enhancing comprises staining the biological tissue with a dye and wherein the dye is selected to have absorption spectrum characteristics corresponding to the frequency of the coherent light beam to maximize absorption of the coherent light by the dye.

31. The method of claim 26 wherein the step of positioning comprises placing the light sensitive recording medium in direct contact with the biological tissue.

32. The method of claim 26 further comprising the step of illuminating the hologram with selected light to reconstruct a holographic image of the biological tissue.

33. The method of claim 32 further comprising the step of microscopically examining the holographic image.

34. The method of claim 33 wherein the selected light is broadband filtered light.

35. The method of claim 33 wherein the selected light has a longer wavelength than the coherent light used to record the hologram thereby reconstructing a magnified holographic image.

36. The method of claim 32 wherein the selected light is white light.

37. The method of claim 32 wherein the selected light is laser light.

38. The method of claim 26 further comprising the steps of converting the hologram into corresponding electronic signals and displaying an image responsive to the corresponding signals.

39. The method of claim 38 further comprising the step of performing image processing of the corresponding electronic signals.

40. The method of claim 26 wherein the step of positioning comprises holding the light sensitive recording medium at an angle to the beam of coherent light.

41. The method of claim 26 wherein the step of directing a coherent light beam comprises directing a beam comprising a plurality of different colors onto the light sensitive recording medium to enable formation of a full color hologram.

42. The method of claim 26 wherein the step of positioning comprising positioning the light sensitive recording medium adjacent to live tissue to obtain an in-vivo hologram.

43. The method of claim 26 wherein the step of contrast enhancing comprises injecting a contrast enhancing medium to enhance features of the biological tissue.

44. The method of claim 26 wherein the step of contrast enhancing comprises contrast enhancement of tissue below the biological tissue surface to enhance holographic recording of features below the surface of the biological tissue.

45. The method of claim 44 wherein the contrast enhancement comprises staining with a dye which penetrates below the surface of the biological tissue.

46. The method of claim 44 wherein the contrast enhancing comprises injecting a dye below the surface of the biological tissue.

47. A method for holographic examination of selected biological tissue comprising the steps of:
 forming a liquid layer on the selected biological tissue;
 positioning a light sensitive recording medium in contact with the liquid layer so as to form a direct liquid interface between the light sensitive medium and the biological tissue;
 directing a coherent light beam onto the light sensitive recording medium in the biological tissue; and
 exposing the light sensitive recording medium to a resulting interference pattern, thereby recording a hologram of the biological tissue.

48. The method of claim 47 wherein the step of exposing comprises the step of exposing the recording medium for an extended period of time sufficient to form a holographic interferogram of the selected biological tissue.

49. The method of claim 47 wherein the step of directing the coherent light beam comprises pulsing the light source at least twice to generate at least two light pulses separated in time to generate a holographic interferogram.

50. The method of claim 47 further comprising the step of contact enhancing by staining the biological tissue with a dye.

51. The method of claim 50 wherein the dye is selected to have absorption spectrum characteristics corresponding to the frequency of the coherent light beam to maximize absorption of the coherent light by the dye.

52. The method of claim 47 further comprising the step of illuminating the hologram with selected light to reconstruct a holographic image of the biological tissue.

53. The method of claim 52 further comprising the step of microscopically examining the holographic 54. The method of claim 52 wherein the selected light is white light.

55. The method of claim 52 wherein the selected light is broadband filtered light.

56. The method of claim 52 wherein the selected light has a longer wavelength than the coherent light used to record the hologram thereby reconstructing a magnified holographic image.

57. The method of claim 47 further comprising the steps of converting the hologram into corresponding electronic signals and displaying an image responsive to the corresponding signals.

58. The method of claim 57 further comprising the step of performing image processing of the corresponding electronic signals.

59. The method of claim 47 wherein the step of positioning comprises holding the light sensitive recording medium at an angle to the beam of coherent light.

60. The method of claim 47 wherein the step of directing a coherent light beam comprises directing a beam comprising a plurality of different colors onto the light sensitive recording medium to enable formation of a full color hologram.

61. A method for holographic examination of biological tissue comprising the steps of:
positioning a light sensitive recording medium within approximately 1 mm or less of the biological tissue;
contrast enhancing selected features of the biological tissue by staining the biological tissue with a dye;
directing a coherent light beam onto the light sensitive recording medium and the biological tissue; and
exposing the light sensitive recording medium to a resulting interference pattern, thereby recording a hologram of the biological tissue.

62. The method of claim 61 wherein the step of exposing comprises the step of exposing the recording medium for an extended period of time sufficient to form a holographic interferogram of the selected biological tissue.

63. The method of claim 61 wherein the step of directing the coherent light beam comprises pulsing the light source at least twice to generate at least two light pulses separated in time to generate a holographic interferogram.

64. The method of claim 61 wherein the step of positioning comprises placing the light sensitive recording medium in direct contact with the biological tissue.

65. The method of claim 61 further comprising the step of illuminating the hologram with selected light to reconstruct a holographic image of the biological tissue.

66. The method of claim 65 further comprising the step of microscopically examining the holographic image.

67. The method of claim 65 wherein the selected light is white light.

68. The method of claim 65 wherein the selected light is broadband filtered light.

69. The method of claim 65 wherein the selected light has a longer wavelength than the coherent light used record the hologram thereby reconstructing a magnified holographic image.

70. The method of claim 61 further comprising the steps of converting the hologram into corresponding electronic signals and displaying an image responsive to the corresponding signals.

71. The method of claim 70 further comprising the step of performing image processing of the corresponding electronic signals.

72. The method of claim 61 wherein the step of positioning comprises holding the light sensitive recording medium at an angle to the beam of coherent light.

73. The method of claim 61 wherein the step of directing a coherent light beam comprises directing a beam comprising a plurality of different colors onto the light sensitive recording medium to enable formation of a full color hologram.

74. The method of claim 61 wherein the step of positioning comprises positioning the light sensitive recording medium adjacent to live tissue to obtain an in-vivo hologram.

75. The method of claim 61 wherein the staining comprises staining below the surface of the biological tissue.

76. The method of claim 75 wherein the staining comprises staining with a dye which penetrates below the surface of the biological tissue.

77. The method of claim 75 wherein the staining comprises injecting a dye below the surface of the biological tissue.

78. A method for holographic examination of biological tissue comprising the steps of:
positioning a light sensitive recording medium in close proximity to the biological tissue;
contrast enhancing selected features of the biological tissue by staining the biological tissue with a dye;
applying a liquid layer between the biological tissue and the recording medium to form a liquid interface between the recording medium and the biological tissue;
directing a coherent light beam onto the light sensitive recording medium and the biological tissue; and
exposing the light sensitive recording medium to a resulting interference pattern, thereby recording a hologram of the biological tissue.

* * * * *